US008704844B2

(12) United States Patent
Fleck et al.

(10) Patent No.: US 8,704,844 B2

(45) Date of Patent: Apr. 22, 2014

(54) POWER SAVING FIELD SEQUENTIAL COLOR

(75) Inventors: Rod G. Fleck, Bellevue, WA (US); Derek Leslie Knee, Fort Collins, CO (US)

(73) Assignee: Microsoft Corporation, Redmond, WA (US)

( * ) Notice: Subject to any disclaimer, the term of this patent is extended or adjusted under 35 U.S.C. 154(b) by 365 days.

(21) Appl. No.: 13/104,264

(22) Filed: May 10, 2011

(65) Prior Publication Data

US 2012/0287142 A1    Nov. 15, 2012

(51) Int. Cl.

| | |
|---|---|
| ***G09G 3/16*** | (2006.01) |
| ***G09G 5/00*** | (2006.01) |
| ***G09G 5/02*** | (2006.01) |
| ***A61B 1/06*** | (2006.01) |
| ***H04N 9/04*** | (2006.01) |
| ***H04N 9/083*** | (2006.01) |
| ***H04N 5/57*** | (2006.01) |
| ***H04N 9/12*** | (2006.01) |
| ***H04N 1/46*** | (2006.01) |
| ***G03F 3/08*** | (2006.01) |
| ***G06K 9/00*** | (2006.01) |
| ***G06K 9/40*** | (2006.01) |

(52) U.S. Cl.

USPC ........... 345/589; 345/606; 345/690; 345/204; 345/48; 348/70; 348/269; 348/271; 348/687; 348/742; 358/512; 358/518; 382/167; 382/254; 382/274; 382/276

(58) Field of Classification Search

USPC ......... 345/581, 589, 600, 606, 612–613, 643, 345/204, 690, 207, 691, 694, 211, 214, 36, 345/39, 45–46, 48, 63, 77, 84, 87–89; 348/68–70, 71, 254, 261, 279, 552, 348/599, 630, 687, 708, 739, 742, 348/800–803; 358/1.9, 509, 512, 516, 358/518–520, 525; 382/162, 167, 254, 274, 382/276

See application file for complete search history.

(56) References Cited

U.S. PATENT DOCUMENTS

| | | | |
|---|---|---|---|
| 7,259,769 | B2 | 8/2007 | Diefenbaugh et al. |
| 7,592,996 | B2 | 9/2009 | Brown Elliott et al. |

(Continued)

OTHER PUBLICATIONS

Greef, et al., “Adaptive dimming and adaptive boosting backlight technologies for LCD-TV systems”, Retrieved at <<http://www.eetindia.co.in/STATIC/PDF/200711/EEIOL_2007NOV14_POW_OPTO_TA_01.pdf?SOURCES=DOWNLOAD>>, Nov. 14, 2007, pp. 1-4.

(Continued)

*Primary Examiner* — Wesner Sajous

(74) *Attorney, Agent, or Firm* — Judy Yee; Micky Minhas

(57) ABSTRACT

In embodiments of power saving field sequential color (FSC), an illumination source illuminates pixels of a displayable image by sequentially generating RGB (red, green, blue) components of a pixel in a timed sequence of field sequential color. The pixels of a displayable image may also include a white component derived from the RGB components. An illumination reduction algorithm is implemented to determine the highest RGB (or RGBW) components from any of the pixels of the displayable image. The highest RGB (or RGBW) components can be determined from any combination of the same or different pixels of the displayable image. The illumination reduction algorithm then divides each of the highest RGB (or RGBW) components by a maximum brightness value to generate respective RGB (or RGBW) component factors. A display controller then processes each pixel of the displayable image for display according to the RGB (or RGBW) component factors.

17 Claims, 5 Drawing Sheets

(56) References Cited

U.S. PATENT DOCUMENTS

| | | | | |
|---|---|---|---|---|
| 2007/0216616 | A1* | 9/2007 | Stessen et al. | 345/84 |
| 2007/0222741 | A1* | 9/2007 | Itaya | 345/102 |
| 2008/0192065 | A1* | 8/2008 | Selbrede et al. | 345/589 |
| 2008/0238856 | A1 | 10/2008 | Bhowmik et al. | |
| 2008/0246782 | A1* | 10/2008 | Endo et al. | 345/690 |
| 2009/0167672 | A1 | 7/2009 | Kerofsky et al. | |
| 2009/0284457 | A1 | 11/2009 | Botzas et al. | |
| 2010/0013748 | A1* | 1/2010 | Cok et al. | 345/83 |
| 2010/0073338 | A1* | 3/2010 | Miller et al. | 345/205 |
| 2011/0115815 | A1* | 5/2011 | Xu et al. | 345/626 |
| 2011/0255013 | A1* | 10/2011 | Selbrede et al. | 348/739 |

OTHER PUBLICATIONS

"VESA Issues Updated Embedded Display Port Standard", Retrieved at <<http://connector.net.tw/index.php/news/277-vesar-issues-updated-embedded-displayport-standard.html>>, Jun. 29, 2010, pp. 2.

Sankar, Ananth, "Content Adaptive LCD Backlight Control", Retrieved at <<http://www.ecnmag.com/Articles/2010/04/Content-Adaptive-LCD-backlight-control/>>, Apr. 16, 2010, pp. 6.

* cited by examiner

POWER SAVING FIELD SEQUENTIAL COLOR

BACKGROUND

A portable device, such as a mobile phone or computer device, may utilize a large amount of power to display a high-quality, full color image. Generally, display technologies either directly generate various colors, such as an OLED display, or use white light through a gating structure, such as through LCD panel cells underneath a color element or color filter, to generate an image. An exception is DLP projection displays that generate various colors utilizing a moving color wheel and fast moving mirrors at a very high refresh rate to avoid color break-up (CBU) which is perceived as image distortion. Other display technologies have attempted to implement high-speed gating techniques with high refresh rates, such as with an LCD panel, without color filters and using sidelit or backlit sets of color LEDs.

Field sequential color (FSC) displays have advantages over traditional LCD displays, or other gated display technologies. An FSC display can operate with less power consumption since up to 70% of lamination can be lost in color filters when converting white light to various primary colors. An FSC display does not use sub-pixels for color generation, and a single pixel structure with a larger aperture provides for increased transmissivity, resulting in further power reductions. However, with an FSC LCD panel, power consumption to drive each of the LEDs and a display controller is higher due to the high-frequency updates that are needed to avoid a user perceiving inter-frame temporal changes.

SUMMARY

This Summary introduces simplified concepts of power saving field sequential color (FSC), and the concepts are further described below in the Detailed Description and/or shown in the Figures. This Summary should not be considered to describe essential features of the claimed subject matter, nor used to determine or limit the scope of the claimed subject matter.

Power saving field sequential color is described. In embodiments, an illumination source illuminates pixels of a displayable image by sequentially generating RGB (red, green, blue) components of a pixel in a timed sequence of field sequential color. The pixels of a displayable image may also include a white component derived from the RGB components. An illumination reduction algorithm is implemented to determine the highest RGB (or RGBW) components from any of the pixels of the displayable image. The highest RGB (or RGBW) components can be determined from any combination of the same or different pixels of the displayable image. The illumination reduction algorithm then divides each of the highest RGB (or RGBW) components by a maximum brightness value to generate respective RGB (or RGBW) component factors. A display controller then processes each pixel of the displayable image for display according to the RGB (or RGBW) component factors.

In other embodiments, each pixel of the displayable image is processed for display according to the RGB (or RGBW) component factors, which includes multiplying each RGB (or RGBW) component of a pixel by the respective RGB (or RGBW) component factor. Each pixel of the displayable image can be illuminated by sequentially generating the red component, the green component, and the blue component (or the RGBW components) in a timed sequence of field sequential color. The power that is utilized to illuminate a pixel is reduced by decreasing the illumination source based on the RGB (or RGBW) component factors to illuminate the respective RGB (or RGBW) components of the pixel. When the RGB components of a pixel include a percentage of the white component, the white component can be compensated for when illuminating the RGB components of the pixel based on the percentage of the white component, and the illumination source can be further decreased when the white component of the pixel is illuminated.

BRIEF DESCRIPTION OF THE DRAWINGS

Embodiments of power saving field sequential color (FSC) are described with reference to the following Figures. The same numbers may be used throughout to reference like features and components that are shown in the Figures.

DETAILED DESCRIPTION

Power saving field sequential color (FSC) is described, and embodiments provide reducing power utilized by backlight unit LEDs to illuminate pixels of an image displayed with an FSC LCD panel, such as a display device integrated in a mobile phone or portable computer device. Backlight unit power consumption can be optimized during the phases of the temporal LED drive cycles with application of an adaptive algorithm for each color LED in RGB (red, green, blue) and RGBW (white) systems to significantly reduce power consumption for scenes and/or images with high content of a specific LED color verses the other driven colors. Further, RGBW (or other combinations with white) FSC displays can further increase white contributions, particularly when other LED colors may be less power efficient. This focuses on the luma values when illuminating a white phase, and lower power chroma values when illuminating the RGB phases. Further, power consumption can be optimized for some images, such as white text on darker backgrounds, by reducing local maximums for short duration pixel patterns (like text).

An illumination reduction algorithm is implemented for gamma correction of each LED color (excluding or including the color white). Thus, black text on a saturated blue background might not require any red, green, or white LED drive power. Accordingly, user interfaces can be designed to use fewer primary colors to reduce power consumption, which is not possible with traditional LCD displays since back light is common for all colors. In implementations, white LEDs may be far more efficient than other color LED solutions, and a percentage of the luminescent content can be shifted from the primary colors (e.g., RGB) to white and further decrease the illumination output of the primary color LEDs. Additionally, with implementation of independent color gamma adjustment, specific types of content, such as text, can be adjusted to lower luma levels or alternate dither patterns independent of other portions of the background. Similarly, further optimizations by content type can be implemented. For example, photo images and videos might leverage more saturated colors, and text-based solutions might use lower color gamut when power is saved using more white LED illumination. Additionally, external environmental factors may allow further color processing to push greater contrast ratios in sunlight.

While features and concepts of power saving field sequential color can be implemented in any number of different devices, systems, and/or configurations, embodiments of power saving field sequential color are described in the context of the following example devices, systems, and methods.

Figure 1:
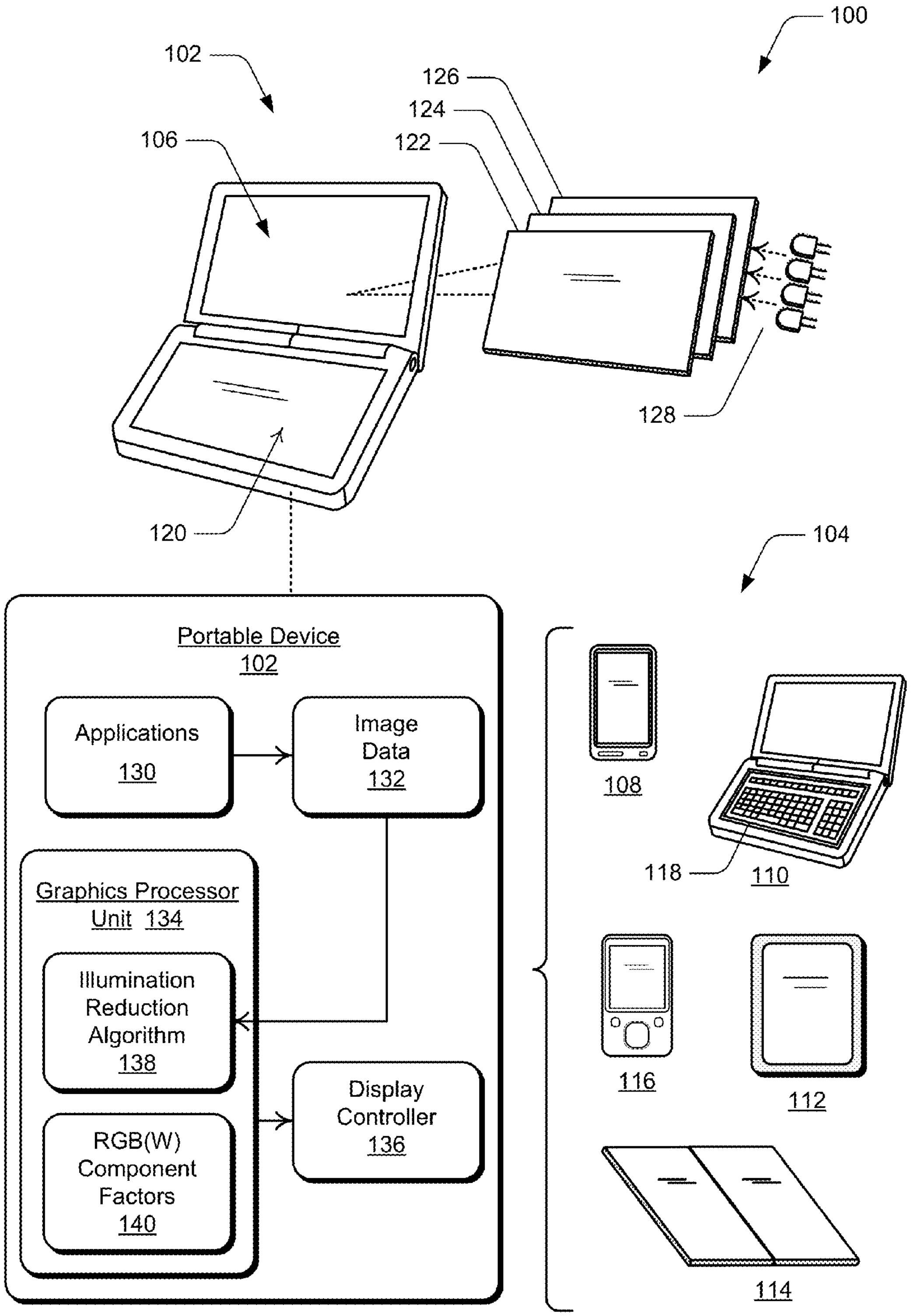
FIG. 1 illustrates an example system that includes a portable device and display assembly in which embodiments of power saving field sequential color can be implemented.

FIG. 1 illustrates an example system 100 in which embodiments of power saving field sequential color can be implemented. The example system includes a portable device 102, which may be configured as any type of computing device 104 that includes a display device 106 as an integrated component of the device. A portable device can be implemented as any one or combination of a mobile phone 108, portable computer 110, tablet device 112, a dual-screen device 114, a media player 116, and/or any other type of consumer electronic device. Any of the various computing devices 104 can be configured as the portable device 102, and may be implemented with various components, such as one or more processors and memory devices, as well as any number and combination of differing components as further described with reference to the example device shown in FIG. 5.

The portable device includes the display device 106, and may include a physical keyboard (shown at 118) or an additional display device (shown at 120) as an integrated component of the portable device. The additional display device may be utilized to display text, graphics, images, user interfaces, and/or a virtual keyboard, such as when an implementation of a portable device does not include a physical keyboard. The display device 106 may be implemented as an FSC LCD panel and can include various display panels and surfaces, such as a display surface 122, a display panel 124, and a backlight assembly 126 (also referred to as a backlight unit (BLU)). The display panel displays images that are viewable through the display surface, and the backlight assembly illuminates the display panel for image display. The backlight assembly includes an illumination source 128, such as LEDs that emit light, as well as a backlight panel or light guide that directs the light to illuminate the display panel, and/or a diffuser that scatters and diffuses the light to uniformly illuminate the display panel.

The portable device 102 can include various applications 130 that generate image data 132. The portable device also includes a graphics processor unit 134 that processes the image data for display as a displayable image on the display device 106 (e.g., the display panel 124). The portable device also includes a display controller 136 that is implemented to control display modes of the display device and drive display content to the display device. In this example, the graphics processor unit includes an illumination reduction algorithm 138 that can be implemented as computer-executable instructions, such as a software application or service, and executed by one or more processors to implement various embodiments of power saving field sequential color.

Figure 2:
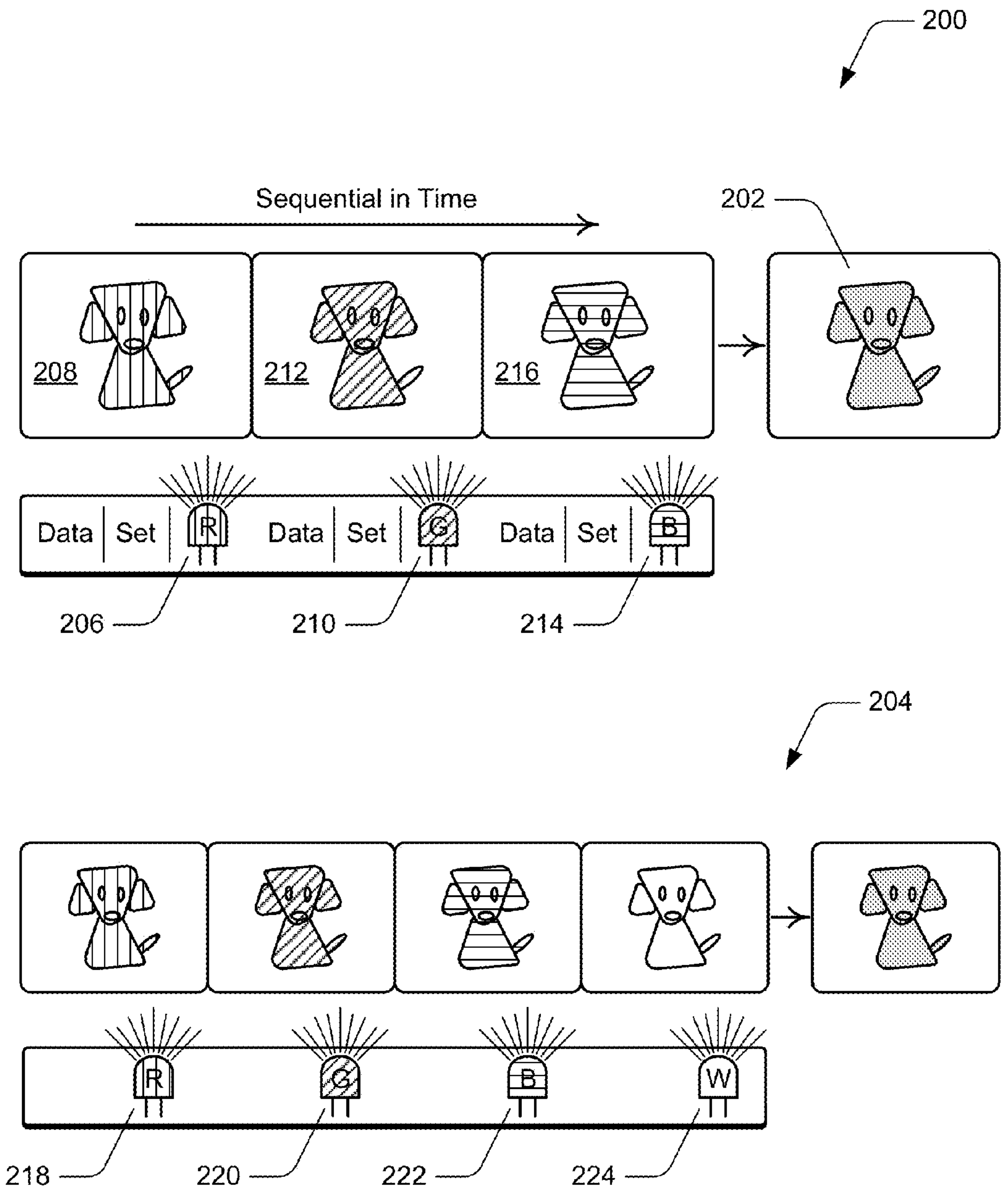
FIG. 2 illustrates examples of field sequential color in accordance with one or more embodiments.

FIG. 2 illustrates examples 200 of generating an image for display utilizing field sequential color (FSC) with RGB (red, green, blue) LEDs. The RGB components that make up a displayable image 202 are sequentially illuminated in a timed sequence, and integrated at the eye of a user over time to perceive the displayed image. An FSC LCD panel can be implemented to sequentially illuminate RGB (red, green, blue) colored LEDs, or RGBW (white) colored LEDs in an embodiment shown at 204. Note that an illumination sequence may be any combination of RGB or RGBW, such as an illumination sequence of RWGB. The FSC LCD panel then lets a designated amount of each color through the display on a pixel-by-pixel basis. A majority of colors can be created with combinations of the RGB LEDs and controlled gating of the FSC LCD panel.

For example, a red LED 206 illuminates the red component of a pixel to display the image at 208 with the appropriate value of red color (i.e., shown as vertical shading in this example merely for descriptive purposes). A green LED 210 then illuminates the green component of the pixel to display the image at 212 with the appropriate value of green color (i.e., shown as diagonal shading in this example merely for descriptive purposes). A blue LED 214 then illuminates the blue component of the pixel to display the image at 216 with the appropriate value of blue color (i.e., shown as horizontal shading in this example merely for descriptive purposes). In the example shown at 204, a red LED 218, a green LED 220, a blue LED 222, and a white LED 224 sequentially illuminate the respective RGBW components of the pixel in a timed sequence of field sequential color to display the image.

Power is used (or consumed) to drive an FSC LCD panel, such as the power used by the display controller 136 (FIG. 1) and the power used for each LED during an ON-phase to illuminate the RGB (or RGBW) components of the pixels for a displayable image. However, the power consumption can be reduced in the backlight unit (BLU) (e.g., the backlight assembly 126 of the display device 106) via more efficient use of the LEDs (e.g., illumination source 128), depending on the brightness of display content. In some video scenes, displayable images, photos, user interfaces, and for text on dark backgrounds, the average brightness of a frame may only be 50% or less on average. When the frame is analyzed, the LED backlight energy can be reduced to levels that match the overall luma requirements for the image. The FSC LCD pixel values (e.g., the opening of the LCD light valves) can then be adjusted to compensate for the backlight reduction of illumination from the LEDs and, in general, a user will not likely perceive any difference in the brightness of a displayed image, but power consumption to illuminate the image is significantly reduced.

In the example system 100 shown in FIG. 1, an application 130 at the portable device 102 generates the image data 132 for a displayable image. The illumination reduction algorithm 138 determines the maximums of specific colors and luma data from the entire image, and the color maximums can then be used to determine the LED power output per color phase. In general, LCD displays are non-linear and a gamma correction algorithm can be used to map linear values from the source to corrected non-linear drive values on the display. The gamma corrected values can then be used to calculate multipliers for LCD pixel openings and corrected LED output.

In embodiments, the illumination reduction algorithm 138 at the example portable device 102 is implemented to determine the highest RGB (red, green, blue) components (0-255 max brightness) from any of the pixels of a displayable image. The highest RGB components can be determined from any combination of the same or different pixels of the displayable image. The illumination reduction algorithm can also determine the highest RGBW (red, green, blue, white) components from any combination of the same or different pixels. For example, the highest red component can be determined from a first pixel of the displayable image, the highest green component can be determined from a different, second pixel of the displayable image, the highest blue component can be determined from a different, third pixel of the displayable image, and/or the highest white component can be determined from a different, fourth pixel of the displayable image.

The illumination reduction algorithm 138 can then divide each of the highest RGB components (or RGBW components) by a maximum brightness value to generate the respective RGB component factors 140 (or RGBW component factors). For example, if a displayable image has a highest blue component of 40%, the blue LED (e.g., illumination source) can be run at only 40% to illuminate the blue components of the pixels for the displayable image, and all of the blue pixel components can be multiplied by 2.5 (i.e., 40% of 255 is a 2.5 component factor). In implementations, the maximum brightness value is 255 from the color pure white, which is the brightest and represented by the RGB values (255, 255, 255). The other end of the spectrum is the color pure black, which is the absence of color represented by the RGB values (0,0,0).

The display controller 136 at the example portable device 102 is implemented to then process each pixel of the displayable image for display according to the RGB component factors 140 (or RGBW component factors). The display controller processing a pixel according to the RGB (or RGBW component factors) is implemented to decrease the illumination source 128 based on the red component factor to illuminate the red component of the pixel, decrease the illumination source based on the green component factor to illuminate the green component of the pixel, decrease the illumination source based on the blue component factor to illuminate the blue component of the pixel, and decrease the illumination source based on the white component factor to illuminate the white component of the pixel. Accordingly, power that is utilized to illuminate the pixel is reduced by decreasing the illumination source based on the respective RGB (or RGBW) component factors when each pixel of the displayable image is illuminated by sequentially generating the red component, the green component, the blue component, and the white component in the timed sequence for field sequential color.

For luminescence, more white illumination from a white LED, or more white derived from a combination of RGB can be implemented to account for color break up, LED efficiency, and accurate color gamma. The illumination reduction algorithm 138 is also implemented to separate luma values from display source RGB values and pixel component output values. This process can also be implemented for an FSC LCD panel with RGBW backlight to allow a single, clear sub-pixel component for luma. A white LED can be included in the illumination source 128 to create a pseudo white subpixel temporally. For RGBW FSC solutions, the illumination reduction algorithm can generate luma contributions with all of the colors, or attribute as much of the luma component to white (e.g., the RGB components of a pixel include a percentage of the white component). In embodiments, the illumination reduction algorithm can compensate for the white component when the RGB components of the pixel are illuminated based on the percentage of the white component that is included in the RGB components.

Additional optimizations to reduce power consumption include expanded analysis of local maximums to determine if only a small percentage of the pixels can be smoothed to a lower maximum (e.g., clipping of the small exceptions). This may distort the displayable image, but a number of higher contrast small zone pixel power reductions may not be perceivable by a user. These optimizations can be applied on a specific content basis, such as for text on a background (e.g., in a browser or email), or for video and photo content. The optimizations can also be applied temporally for video image types where frame rates may further reduce a user's ability to perceive smaller maximums, which are temporally short in time (e.g., under 3 frames). These power saving techniques can also be used with specific content types, such as for text on a darker background, to also reduce backlight power by reducing local maximums (like those of text) across small distances (e.g., reduce the contrast ratio of text with lighter text by smoothing local maximums). Further, the power saving techniques can be implemented to optimize a user interface selection of primary colors, reduce color components (e.g., lower pixel brightness) with higher contrast color selection, and for stronger dithering of text to reduce color content. Further, selecting colors which have a higher perceived sensitivity allow reducing other color components.

Example methods 300 and 400 are described with reference to FIGS. 3 and 4 in accordance with one or more embodiments of power saving field sequential color. Generally, any of the services, functions, methods, procedures, components, and modules described herein can be implemented using software, firmware, hardware (e.g., fixed logic circuitry), manual processing, or any combination thereof. A software implementation represents program code that performs specified tasks when executed by a computer processor. The example methods may be described in the general context of computer-executable instructions, which can include software, applications, routines, programs, objects, components, data structures, procedures, modules, functions, and the like. The program code can be stored in one or more computer-readable storage media devices, both local and/or remote to a computer processor. The methods may also be practiced in a distributed computing environment by multiple computer devices. Further, the features described herein are platform-independent and can be implemented on a variety of computing platforms having a variety of processors.

Figure 3:
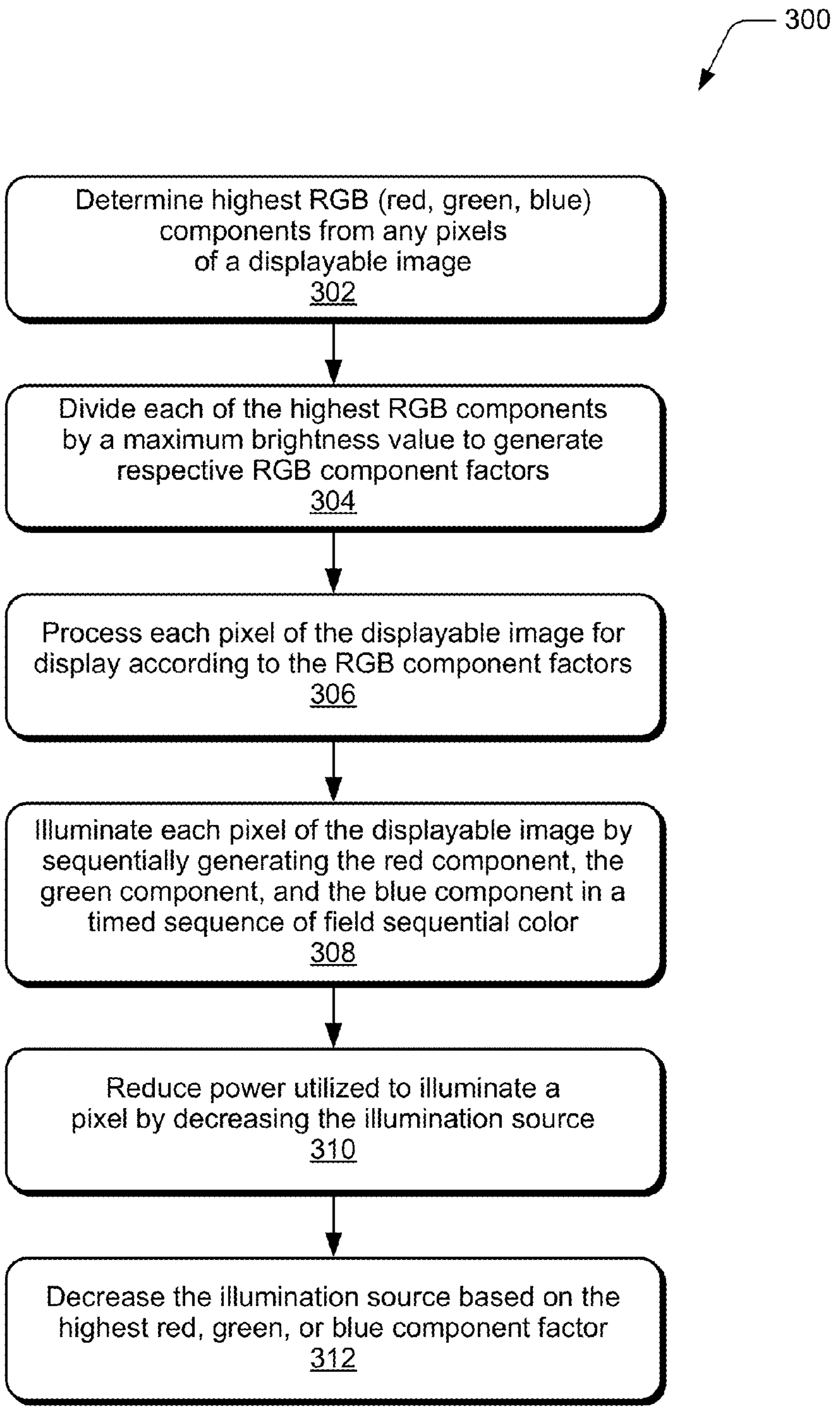
FIG. 3 illustrates example method(s) of power saving field sequential color in accordance with one or more embodiments.

FIG. 3 illustrates example method(s) 300 of power saving field sequential color. The order in which the method blocks are described are not intended to be construed as a limitation, and any number of the described method blocks can be combined in any order to implement a method, or an alternate method.

At block 302, highest RGB (red, green, blue) components are determined from any pixels of a displayable image. For example, the illumination reduction algorithm 138 at the example portable device 102 (FIG. 1) determines the highest RGB (red, green, blue) components (0-255 max brightness) from any of the pixels of a displayable image. Each of the pixels of the displayable image can include RGB components, and the highest RGB components can be determined from any combination of the same or different pixels. For example, the illumination reduction algorithm determines the highest red component from a first pixel of the displayable image, determines the highest green component from a different, second pixel of the displayable image, and determines the highest blue component from a different, third pixel of the displayable image.

At block 304, each of the highest RGB components are divided by a maximum brightness value to generate respective RGB component factors. For example, the illumination reduction algorithm 138 then divides each of the determined highest RGB components by a maximum brightness value (e.g., 255) to generate the respective RGB component factors 140.

At block 306, each pixel of the displayable image is processed for display according to the RGB component factors. For example, the display controller 136 at the example portable device 102 processes each pixel of the displayable image for display according to the generated RGB component factors. The processing includes multiplying the red component of a pixel by the red component factor, multiplying the green component of the pixel by the green component factor, and multiplying the blue component of the pixel by the blue component factor.

At block 308, each pixel of the displayable image is illuminated by sequentially generating the red component, the green component, and the blue component in a timed sequence of field sequential color. At block 310, power utilized to illuminate a pixel is reduced by decreasing the illumination source. For example, the display controller 136 decreases the illumination source 128 based on the red component factor to illuminate the red component of a pixel, based on the green component factor to illuminate the green component of the pixel, and based on the blue component factor to illuminate the blue component of the pixel. The illumination source includes the red LED 206 (FIG. 2), the green LED 210, and the blue LED (214) that sequentially illuminate an FSC LCD panel (e.g., the display device 106) when the LEDs are initiated in any order to illuminate the LCD panel.

At block 312, the illumination source is decreased based on the highest red, green, or blue component factor. For example, the display controller 136 decreases the illumination source 128 based on the overall highest RGB component factor 140.

Figure 4:
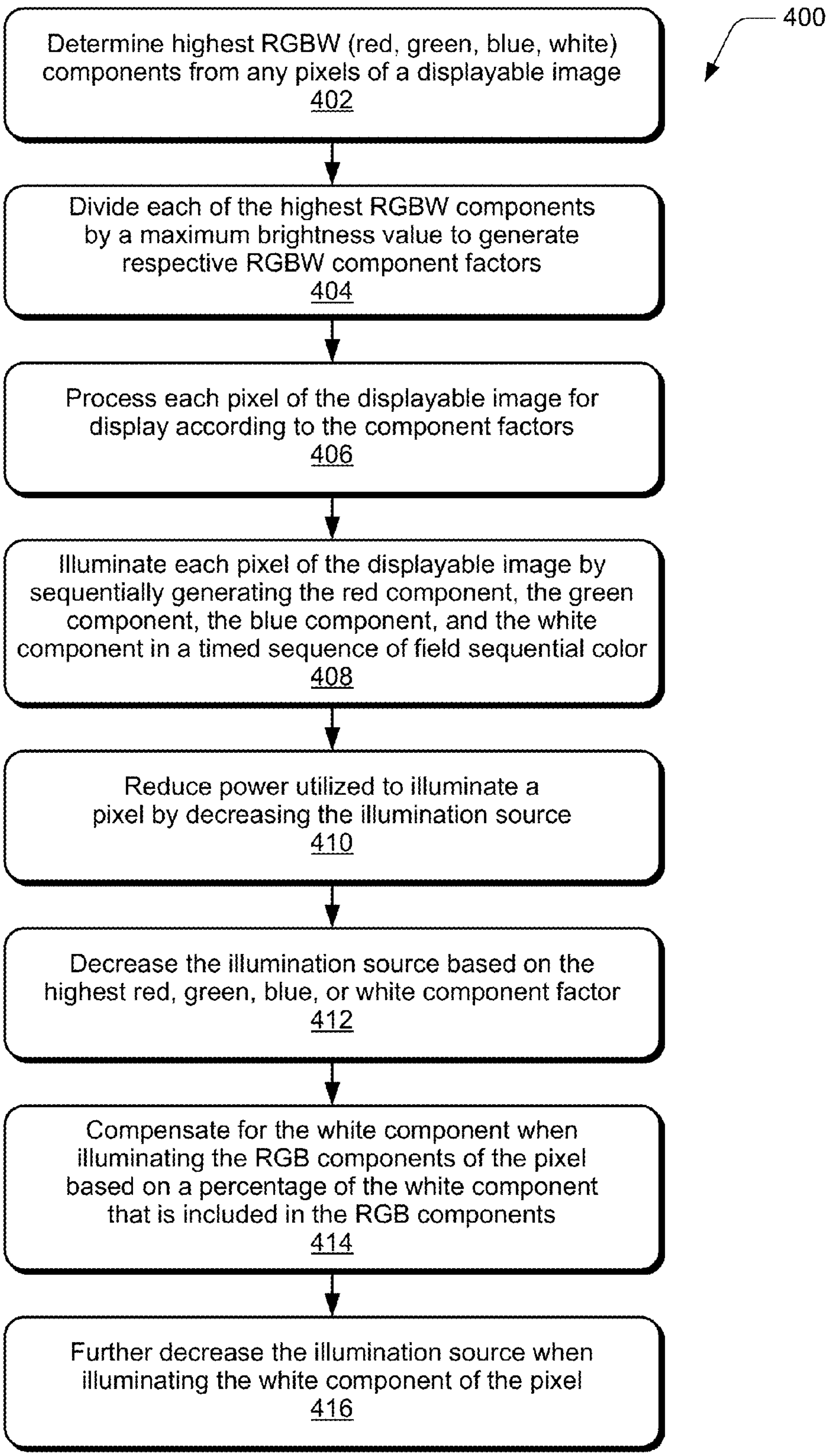
FIG. 4 illustrates example method(s) of power saving field sequential color in accordance with one or more embodiments.

FIG. 4 illustrates example method(s) 400 of power saving field sequential color. The order in which the method blocks are described are not intended to be construed as a limitation, and any number of the described method blocks can be combined in any order to implement a method, or an alternate method.

At block 402, highest RGBW (red, green, blue, white) components are determined from any pixels of a displayable image. For example, the illumination reduction algorithm 138 at the example portable device 102 (FIG. 1) determines the highest RGBW (red, green, blue, white) components (0-255 max brightness) from any of the pixels of a displayable image. Each of the pixels of the displayable image can include RGB components, and a white component can be derived from the RGB components. The highest RGBW components can be determined from any combination of the same or different pixels. For example, the illumination reduction algorithm determines the highest red component from a first pixel of the displayable image, determines the highest green component from a different, second pixel of the displayable image, determines the highest blue component from a different, third pixel of the displayable image, and/or determines the highest white component from a different, fourth pixel of the displayable image.

At block 404, each of the highest RGBW components are divided by a maximum brightness value to generate respective RGBW component factors. For example, the illumination reduction algorithm 138 then divides each of the determined highest RGBW components by a maximum brightness value (e.g., 255) to generate the respective RGBW component factors 140.

At block 406, each pixel of the displayable image is processed for display according to the component factors. For example, the display controller 136 at the example portable device 102 processes each pixel of the displayable image for display according to the generated RGBW component factors. The processing includes multiplying the red component of a pixel by the red component factor, multiplying the green component of the pixel by the green component factor, multiplying the blue component of the pixel by the blue component factor, and multiplying the white component of the pixel by the white component factor.

At block 408, each pixel of the displayable image is illuminated by sequentially generating the red component, the green component, the blue component, and the white component in a timed sequence of field sequential color. At block 410, power utilized to illuminate a pixel is reduced by decreasing the illumination source. For example, the display controller 136 decreases the illumination source 128 based on the red component factor to illuminate the red component of a pixel, based on the green component factor to illuminate the green component of the pixel, based on the blue component factor to illuminate the blue component of the pixel, and based on the white component factor to illuminate the white component of the pixel. The illumination source includes the red LED 218, the green LED 220, the blue LED 222, and the white LED 224 that sequentially illuminate an FSC LCD panel (e.g., the display device 106).

At block 412, the illumination source is decreased based on the highest red, green, blue, or white component factor. For example, the display controller 136 decreases the illumination source 128 based on the overall highest RGBW component factor 140. At block 414, the white component is compensated for when illuminating the RGB components of a pixel based on a percentage of the white component that is included in the RGB components. For example, the illumination reduction algorithm 138 can compensate for the white component derived from the RGB components when the RGB components of a pixel are illuminated based on the percentage of the white component that is included in the RGB components. At block 416, the illumination source is further decreased when illuminating the white component of the pixel. For example, the display controller 136 further decreases the illumination source when illuminating the white component which is already a percentage of the illuminated RGB components.

Figure 5:
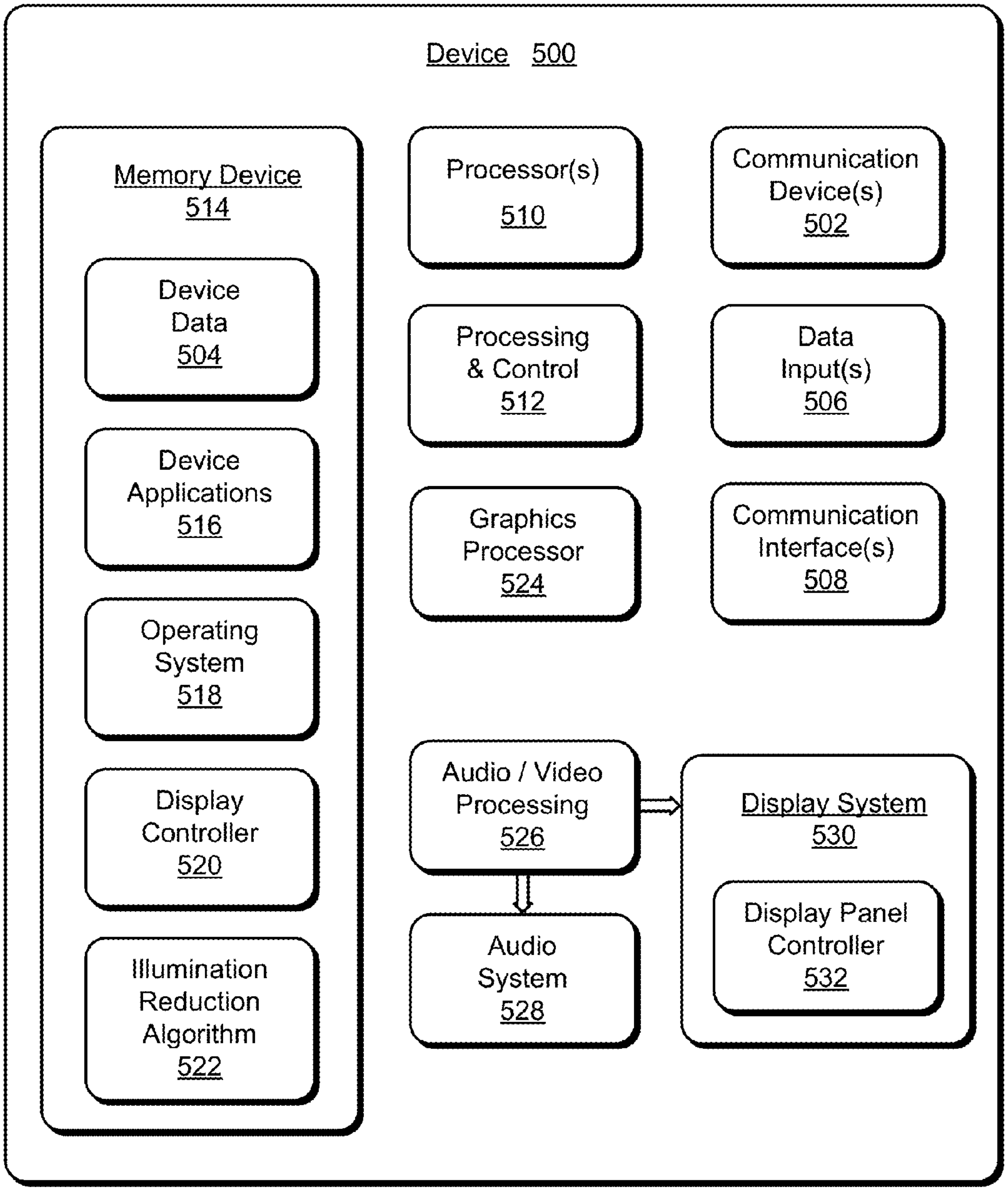
FIG. 5 illustrates various components of an example device that can implement embodiments of power saving field sequential color.

FIG. 5 illustrates various components of an example device 500 that can be implemented as any of the devices, or services implemented by devices, described with reference to the previous FIGS. 1-4. In embodiments, the device may be implemented as any one or combination of a fixed or mobile device, in any form of a consumer, computer, server, portable, user, communication, phone, navigation, television, appliance, gaming, media playback, and/or electronic device. The device may also be associated with a user (i.e., a person) and/or an entity that operates the device such that a device describes logical devices that include users, software, firmware, hardware, and/or a combination of devices.

The device 500 includes communication devices 502 that enable wired and/or wireless communication of device data 504, such as received data, data that is being received, data scheduled for broadcast, data packets of the data, etc. The device data or other device content can include configuration settings of the device, media content stored on the device, and/or information associated with a user of the device. Media content stored on the device can include any type of audio, video, and/or image data. The device includes one or more data inputs 506 via which any type of data, media content, and/or inputs can be received, such as user-selectable inputs, messages, communications, music, television content, recorded video content, and any other type of audio, video, and/or image data received from any content and/or data source.

The device 500 also includes communication interfaces 508, such as any one or more of a serial, parallel, network, or wireless interface. The communication interfaces provide a connection and/or communication links between the device and a communication network by which other electronic, computing, and communication devices communicate data with the device.

The device 500 includes one or more processors 510 (e.g., any of microprocessors, controllers, and the like) which process various computer-executable instructions to control the operation of the device. Alternatively or in addition, the device can be implemented with any one or combination of software, hardware, firmware, or fixed logic circuitry that is implemented in connection with processing and control circuits which are generally identified at 512. Although not shown, the device can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

The device 500 also includes one or more memory devices 514 (e.g., computer-readable storage media) that enable data storage, such as random access memory (RAM), non-volatile memory (e.g., read-only memory (ROM), flash memory, etc.), and a disk storage device. A disk storage device may be implemented as any type of magnetic or optical storage device, such as a hard disk drive, a recordable and/or rewriteable disc, and the like. The device may also include a mass storage media device.

Computer readable media can be any available medium or media that is accessed by a computing device. By way of example, and not limitation, computer readable media may comprise storage media and communication media. Storage media include volatile and non-volatile, removable and non-removable media implemented in any method or technology for storage of information, such as computer-readable instructions, data structures, program modules, or other data. Storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by a computer.

Communication media typically embody computer-readable instructions, data structures, program modules, or other data in a modulated data signal, such as carrier wave or other transport mechanism. Communication media also include any information delivery media. The term modulated data signal means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

A memory device 514 provides data storage mechanisms to store the device data 504, other types of information and/or data, and various device applications 516. For example, an operating system 518 and a display controller 520 can be maintained as a software application with a memory device and executed on the processors. The device applications may also include a device manager, such as any form of a control application, software application, signal processing and control module, code that is native to a particular device, a hardware abstraction layer for a particular device, and so on. In this example, the device applications include an illumination reduction algorithm 522. The illumination reduction algorithm is shown as software and/or computer application. Alternatively or in addition, the analysis algorithm can be implemented as hardware, software, firmware, fixed logic, or any combination thereof.

The device 500 also includes a graphics processor 524, and includes an audio and/or video processing system 526 that generates audio data for an audio system 528 and/or generates display data for a display system 530. The audio system and/or the display system may include any devices that process, display, and/or otherwise render audio, video, display, and/or image data. For example, the display system includes a display panel controller 532. Display data and audio signals can be communicated to an audio device and/or to a display device via an RF (radio frequency) link, S-video link, composite video link, component video link, DVI (digital video interface), analog audio connection, or other similar communication link. In implementations, the audio system and/or the display system are external components to the device. Alternatively, the audio system and/or the display system are integrated components of the example device.

Although embodiments of power saving field sequential color have been described in language specific to features and/or methods, the subject of the appended claims is not necessarily limited to the specific features or methods described. Rather, the specific features and methods are disclosed as example implementations of power saving field sequential color.

The invention claimed is:

1. A method, comprising:

determining, using a computing device, highest RGB (red, green, blue) components from any pixels of a displayable image, each of the pixels of the displayable image including RGB components;

dividing, using the computing device, each of the highest RGB components by a maximum brightness value to generate respective RGB component factors;

processing, using the computing device, each pixel of the displayable image for display according to the RGB component factors; and further comprising:

illuminating, using the computing device, each pixel of the displayable image by sequentially generating the red component, the green component, and the blue component in a timed sequence of field sequential color, and reducing power utilized to illuminate the pixel by:

decreasing an illumination source based on the red component factor to illuminate the red component of the pixel;

decreasing the illumination source based on the green component factor to illuminate the green component of the pixel; and decreasing the illumination source based on the blue component factor to illuminate the blue component of the pixel, wherein the illumination source comprises a red LED, a green LED, and a blue LED that sequentially illuminate an LCD panel of a display device when the LEDs are initiated in any order to illuminate the LCD panel.

2. A method as recited in claim 1, wherein said determining the highest RGB components includes:

determining the highest red component from a first pixel of the displayable image;

determining the highest green component from a different, second pixel of the displayable image; and determining the highest blue component from a different, third pixel of the displayable image.

3. A method as recited in claim 1, further comprising:

determining a highest white component from any of the pixels of the displayable image, each of the pixels of the displayable image including a white component derived from the RGB components;

dividing the highest white component by the maximum brightness value to generate a white component factor; and further processing each pixel of the displayable image for display according to the white component factor.

4. A method as recited in claim 3, wherein said processing each pixel of the displayable image for display includes:

multiplying the red component of a pixel by the red component factor;

multiplying the green component of the pixel by the green component factor;

multiplying the blue component of the pixel by the blue component factor; and multiplying the white component of the pixel by the white component factor.

5. A method as recited in claim 4, wherein the illuminating each pixel of the displayable image further comprises generating, as part of said sequentially generating, the white component in the timed sequence of field sequential color, and said reducing power utilized to illuminate the pixel is performed by decreasing an illumination source based on the respective RGBW component factors.

6. A method as recited in claim 5, wherein the RGB components of the pixel include a percentage of the white component, the method further comprising:

decreasing the illumination source when said illuminating the white component of the pixel; and compensating for the white component when said illuminating the RGB components of the pixel based on the percentage of the white component that is included in the RGB components.

7. A method as recited in claim 5, wherein said decreasing the illumination source based on the respective RGBW component factors includes decreasing the illumination source based on the highest red, green, blue, or white component factor.

8. A device, comprising:

an illumination source configured to illuminate pixels of a displayable image by sequentially generating RGB (red, green, blue) components of a pixel in a timed sequence of field sequential color;

a display controller configured to process each pixel of the displayable image for display according to RGB component factors; and a memory and a processor to implement an illumination reduction algorithm that is configured to:

determine highest RGB components from any of the pixels of the displayable image; and divide each of the highest RGB components by a maximum brightness value to generate the respective RGB component factors wherein the illumination reduction algorithm is further configured to:

determine the highest red component from a first pixel of the displayable image;

determine the highest green component from a different, second pixel of the displayable image; and determine the highest blue component from a different, third pixel of the displayable image.

9. A device as recited in claim 8, wherein the display controller is further configured to:

decrease the illumination source based on the red component factor to illuminate the red component of the pixel;

decrease the illumination source based on the green component factor to illuminate the green component of the pixel; and decrease the illumination source based on the blue component factor to illuminate the blue component of the pixel.

10. A device as recited in claim 9, wherein:

the illumination reduction algorithm is further configured to:

determine a highest white component from any of the pixels of the displayable image, each of the pixels of the displayable image including a white component derived from the RGB components;

divide the highest white component by the maximum brightness value to generate a white component factor;

the display controller is further configured to:

process each of the pixels of the displayable image for display according to the white component factor; and decrease the illumination source based on the white component factor to illuminate the white component of the pixel.

11. A device as recited in claim 10, wherein power that is utilized to illuminate the pixel is reduced by decreasing the illumination source based on the respective RGBW component factors when each pixel of the displayable image is illuminated by sequentially generating the red component, the green component, the blue component, and the white component in the timed sequence of field sequential color.

12. A device as recited in claim 10, wherein the RGB components of the pixel include a percentage of the white component, and wherein:

the illumination reduction algorithm is further configured to compensate for the white component when the RGB components of the pixel are illuminated based on the percentage of the white component that is included in the RGB components; and the display controller is further configured to further decrease the illumination source when the white component of the pixel is illuminated.

13. One or more computer-readable storage media devices comprising instructions that are executable and, responsive to executing the instructions, a computing device:

determines highest RGBW (red, green, blue, white) components from any pixels of a displayable image, each of the pixels of the displayable image including RGBW components;

divides each of the highest RGBW components by a maximum brightness value to generate respective RGBW component factors; and processes each pixel of the displayable image for display according to the RGBW component factors.

14. One or more computer-readable storage media devices as recited in claim 13, further comprising additional instructions that are executable and, responsive to executing the additional instructions, the computing device:

determines the highest red component from a first pixel of the displayable image;

determines the highest green component from a different, second pixel of the displayable image;

determines the highest blue component from a different, third pixel of the displayable image; and determines the highest white component from a different, fourth pixel of the displayable image.

15. One or more computer-readable storage media devices as recited in claim 13, further comprising additional instructions that are executable and, responsive to executing the additional instructions, the computing device illuminates each pixel of the displayable image by sequentially generating the red component, the green component, the blue component, and the white component in a timed sequence of field sequential color.

16. One or more computer-readable storage media devices as recited in claim 13, further comprising additional instructions that are executable and, responsive to executing the additional instructions to process each pixel of the displayable image for display, the computing device:

multiplies the red component of a pixel by the red component factor, and decreases an illumination source based on the red component factor to illuminate the red component of the pixel;

multiplies the green component of the pixel by the green component factor, and decreases the illumination source based on the green component factor to illuminate the green component of the pixel;

multiplies the blue component of the pixel by the blue component factor, and decreases the illumination source based on the blue component factor to illuminate the blue component of the pixel; and multiplies the white component of the pixel by the white component factor, and decreases the illumination source based on the white component factor to illuminate the white component of the pixel.

17. One or more computer-readable storage media devices as recited in claim 16, further comprising additional instructions that are executable and, responsive to executing the additional instructions, the computing device:

compensates for the white component when the RGB components of the pixel are illuminated based on a percentage of the white component that is included in the RGB components; and further decreases the illumination source when the white component of the pixel is illuminated.

* * * * *